United States Patent
Kroll et al.

(10) Patent No.: US 6,314,319 B1
(45) Date of Patent: *Nov. 6, 2001

(54) METHOD AND APPARATUS FOR TEMPORARILY ELECTRICALLY FORCING CARDIAC OUTPUT IN A TACHYARRHYTHMIA PATIENT

(75) Inventors: Kai Kroll; Mark W. Kroll, both of Minnetonka, MN (US)

(73) Assignee: Galvani, Ltd., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/251,553

(22) Filed: Feb. 17, 1999

Related U.S. Application Data

(63) Continuation of application No. 08/754,712, filed on Dec. 6, 1996, now Pat. No. 5,978,703, which is a continuation of application No. 08/543,001, filed on Oct. 13, 1995, now abandoned, which is a continuation of application No. 08/251,349, filed on May 31, 1994, now abandoned.

(51) Int. Cl.[7] ...................................... A61N 1/39
(52) U.S. Cl. ................................................................. 607/5
(58) Field of Search .............................................. 607/4, 5

(56) References Cited

U.S. PATENT DOCUMENTS 5,193,535 * 3/1993 Bardy et al. ......................... 607/604

* cited by examiner

Primary Examiner—William E. Kamm
(74) Attorney, Agent, or Firm—Fredrikson & Byron, P.A.

(57) ABSTRACT

An electrical method and apparatus for stimulating cardiac cells causing contraction to force hemodynamic output during fibrillation, hemodynamically compromising tachycardia, or asystole. Forcing fields are applied to the heart to give cardiac output on an emergency basis until the arrhythmia ceases or other intervention takes place. The device is used as a stand alone external or internal device, or as a backup to an ICD, atrial defibrillator, or an anti-tachycardia pacemaker. The method and apparatus maintain some cardiac output and not necessarily defibrillation.

101 Claims, 11 Drawing Sheets

METHOD AND APPARATUS FOR TEMPORARILY ELECTRICALLY FORCING CARDIAC OUTPUT IN A TACHYARRHYTHMIA PATIENT

This application is a continuation of Ser. No. 08/754,712 filed Dec. 6, 1996, now U.S. Pat. No. 5,978,703 which is a continuation of Ser. No. 08/543,001 filed Oct. 13, 1995, now abandoned, which is a continuation of Ser. No. 08/251,349 filed May 31, 1994, now abandoned.

BACKGROUND OF THE INVENTION

1. Field of the Invention

The invention relates to the field of therapies for cardiac arrhythmias, and more particularly, to a method and an apparatus for forcing cardiac output by delivering a pulsatile electrical field to the heart during fibrillation or a hemodynamically compromising tachycardia.

2. Background Information

Approximately 400,000 Americans succumb to ventricular fibrillation each year. It is known that ventricular fibrillation, a usually fatal heart arrhythmia, can only be terminated by the application of an electrical shock delivered to the heart. This is through electrodes applied to the chest connected to an external defibrillator or electrodes implanted within the body connected to an implantable cardioverter defibrillator (ICD). Paramedics cannot usually respond rapidly enough with their external defibrillators to restore life. New methods of dealing with this problem include less expensive external defibrillators (and thus more readily available) and smaller implantable defibrillators. Since the first use on humans of a completely implantable cardiac defibrillator in 1980, research has focused on making them continually smaller and more efficient by reducing the defibrillation threshold energy level. The goal has been to reduce the size of the implantable device so that it could be implanted prophylactically, i.e., in high risk patients before an episode of ventricular fibrillation.

An ICD includes an electrical pulse generator and an arrhythmia detection circuit coupled to the heart by a series of two or more electrodes implanted in the body. A battery power supply, and one or more charge storage capacitors are used for delivering defibrillation shocks in the form of electrical current pulses to the heart. These devices try to restore normal rhythm from the fibrillation. While it works well at restoring normal function, the ICD is large in size and not practical for a truly prophylactic device. A small device capable of maintaining minimal cardiac output, in high risk patients, prior to admission into an emergency room is needed.

In addition, external defibrillators are limited in their performance. The typical paramedic defibrillation may be delayed by 10 minutes. At this time defibrillation may be irrelevant since the rhythm is often advanced to asystole. In asystole, there is little or no electrical activity and certainly no cardiac pumping.

There is a need for a new method and apparatus for dealing with ventricular fibrillation. The defibrillation approach does not work satisfactorily. External devices are too slow in arrival and implantable defibrillators are excessively large (and expensive) for prophylactic use.

SUMMARY OF THE INVENTION

The invention provides an electrical method of stimulating cardiac cells causing contraction to force hemodynamic output during fibrillation, hemodynamically compromising tachycardia, or asystole. Forcing fields are applied to the heart to give cardiac output on an emergency basis until the arrhythmia ceases or other intervention takes place. The device is usable as a stand alone external or internal device or as a backup to an ICD, atrial defibrillator, or an antitachycardia pacemaker.

The goal of the invention is maintaining some cardiac output and not necessarily defibrillation. The method is referred to as Electrical Cardiac Output Forcing and the apparatus is the Electrical Cardiac Output Forcer (ECOF).

In the implantable embodiment, a forcing field is generated by applying approximately 50 volts to the heart at a rate of approximately 100–180 beats per minute. These fields are applied after detection of an arrhythmia and maintained for up to several hours. This will generate a cardiac output which is a fraction of the normal maximum capacity. The heart has a 4 or 5 times reserve capacity so a fraction of normal pumping activity will maintain life and consciousness.

The implantable embodiment is implanted in high risk patients who have never had fibrillation. If they do fibrillate, the ECOF device forces a cardiac output for a period of up to several hours, thus giving the patient enough time to get to a hospital. That patient would then be a candidate for an implantable cardioverter defibrillator (ICD). The ECOF differs from the ICD in that it is primarily intended for a single usage in forcing cardiac output over a period of hours, while the ICD is designed to furnish hundreds of defibrillation shocks over a period of years.

Insofar as is known, no prior attempts have been made at forcing pulses during any type of fibrillation. Some workers in the field have experimented for research purposes with local pacing during fibrillation. For example, Kirchhof did local pacing during atrial fibrillation in dog hearts (Circulation 1993; 88: 736–749). He used 0.5 mm diameter electrodes and pacing stimuli. As expected, small areas around the heart were captured but no pumping action was expected or detected. Similar results have been obtained in the ventricle by KenKnight (Journal of the American College of Cardiology 1994; 283A).

Various researchers have tried multiple pulse defibrillation without success in reducing the energy thresholds, for example, Schuder (Cardiovascular Research; 1970, 4, 497–501), Kugelberg (Medical & Biological Engineering; 1968, 6, 167–169 and Acta Chirurgica Scandinavia; 1967, 372), Resnekov (Cardiovascular Research; 1968, 2, 261–264), and Geddes (Journal of Applied Physiology; 1973, 34, 8–11).

More recently, Sweeney (U.S. Pat. No. 4,996,984) has experimented with multiple (primarily dual) shocks of timing calculated from the fibrillation rate. None of these approaches has been able to significantly reduce voltages from conventional defibrillation shocks. Importantly, none of these approaches anticipated the idea that the individual pulses might force cardiac output or could sustain life indefinitely.

Some have considered the use of smaller pulses, before the shock, to reduce the energy required for a defibrillation shock (Kroll, European Application No. 540266), but never anticipated eliminating the defibrillation shock itself or anticipated that the pulses themselves could maintain cardiac output. Some have suggested using higher voltage pulses to terminate ventricular tachycardias, but no suggestion was made of an application with fibrillation or of obtaining cardiac output (Kroll WO 93/19809) and Duffin (WO 93/06886).

The benefits of this invention will become clear from the following description by reference to the drawings.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, applicants provide these embodiments so that this disclosure will be thorough and complete, and will convey the scope of the invention to those skilled in the art.

Figure 1:
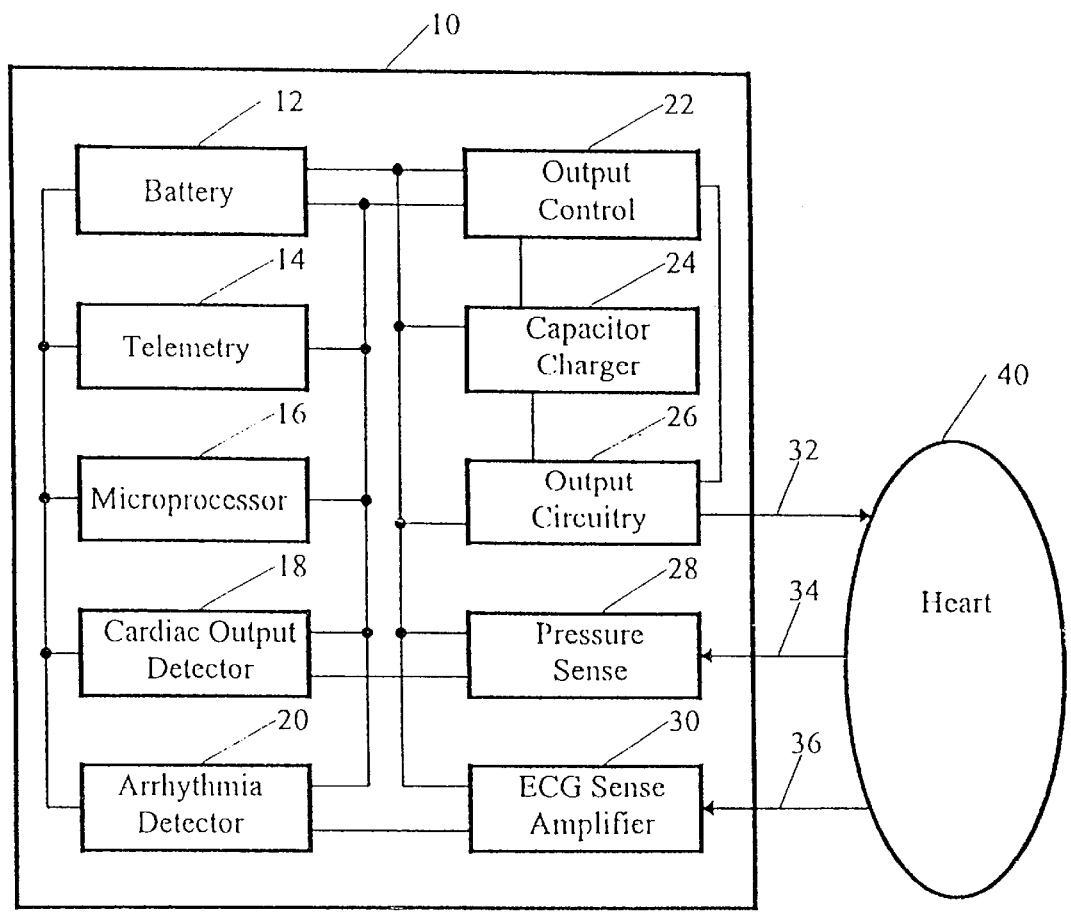
FIG. 1 is a block diagram illustrating a system constructed in accordance with the principles of the present invention.

FIG. 1 is a block diagram illustrating a system 10 constructed in accordance with the principles of the present invention. The device circuitry is connected to the heart 40 via a series of leads; output lead 32, pressure sense lead 34, and ECG sense lead 36. The electronic circuit includes a conventional ECG amplifier 30 for amplifying cardiac signals. The amplified cardiac signals are analyzed by a conventional arrhythmia detector 20 which determines if an arrhythmia is present. The arrhythmia detector 20 may be one of several types well known to those skilled in the art and is preferably able to distinguish between different types of arrhythmias. For example; fibrillation, tachycardia or asystole. The circuit also contains an optional pressure sensing section 28 which amplifies and conditions a signal from an optional pressure sensor from within the heart or artery. The output of the pressure sense circuit 28 is fed to a cardiac output detection circuit 18 which analyzes the data and determines an estimate of the cardiac output. Data from the arrhythmia detector circuit 20 and the cardiac output detection circuit 18 is fed to the microprocessor 16. The microprocessor 16 determines if Electrical Cardiac Output Forcing (ECOF) is appropriate. If forcing is indicated, the microprocessor 16 prompts the output control 22 to charge a capacitor within the output circuit 26 via the capacitor charger 24. The output control 22 directs the output circuitry 26 to deliver the pulses to the heart 40 via the output leads 32. The microprocessor 16 may communicate with external sources via a telemetry circuit 14 within the device 10. The power for the device 10 is supplied by an internal battery 12.

Figure 2A:
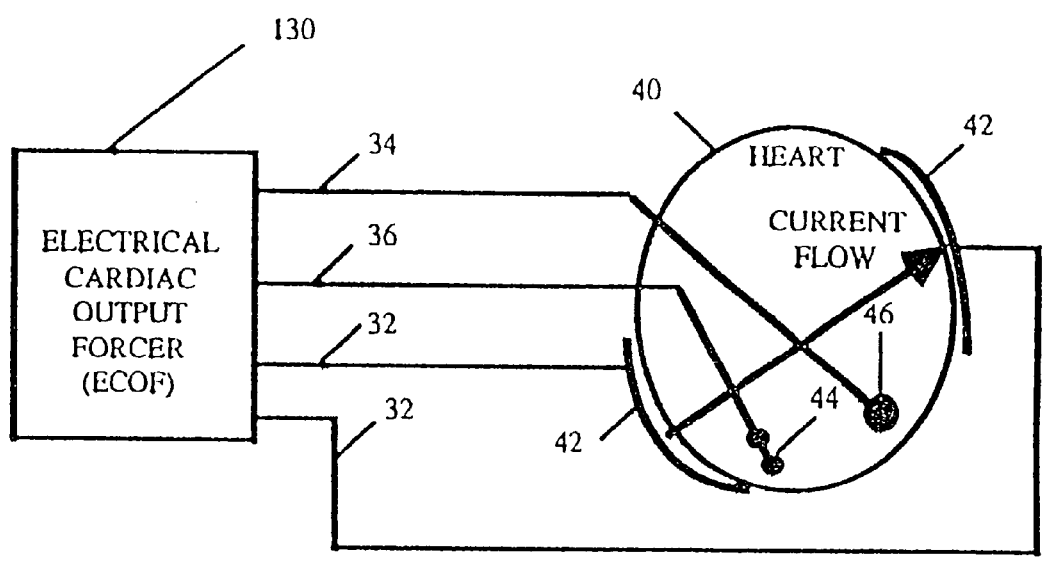
FIG. 2a shows the connection of an implantable embodiment of the device to the heart in an epicardial patch configuration.

FIG. 2a is a diagram showing the connection of an implantable embodiment of the device 130 to the heart 40 in an epicardial patch configuration. In this thoracotomy configuration, current passes through an output lead pair 32 to electrode patches 42 which direct the current through the heart 40. There is an optional pressure sense lead 34 which passes the signal from an optional pressure transducer 46 which lies in the heart 40. The ECG is monitored by sense electrodes 44 and passed to the device 130 by a lead 36. The area of the electrodes 42 is at least 0.5 cm². The size of the electrode is greater than that of a pacing lead and no more than that of a defibrillation electrode or between approximately 0.5 cm² and 20 cm² each.

Figure 2B:
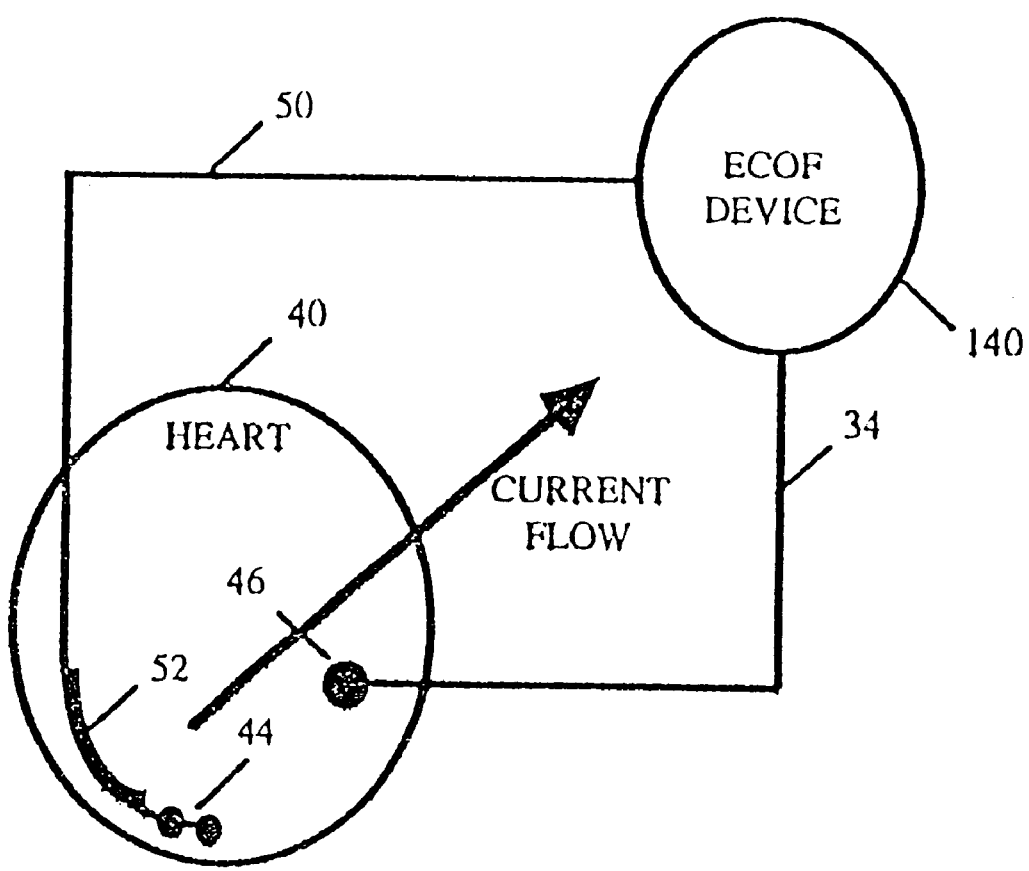
FIG. 2b shows the connection of an implantable embodiment of the device to the heart using an endocardial lead system and the device housing as an electrode.

FIG. 2b shows a non-thoracotomy system embodiment of the invention. In this system, the current passes from a coil electrode 52 in the heart 40 to the housing of the device 140. An endocardial lead 50 combines the ECG sensing lead and the pulse output lead. The ECG is monitored by sense electrodes 44 in the heart 40 and passes through the endocardial lead 50. There is an optional pressure transducer 46 in the heart 40 which passes a signal to the device 140 via optional lead 34.

Figure 3:
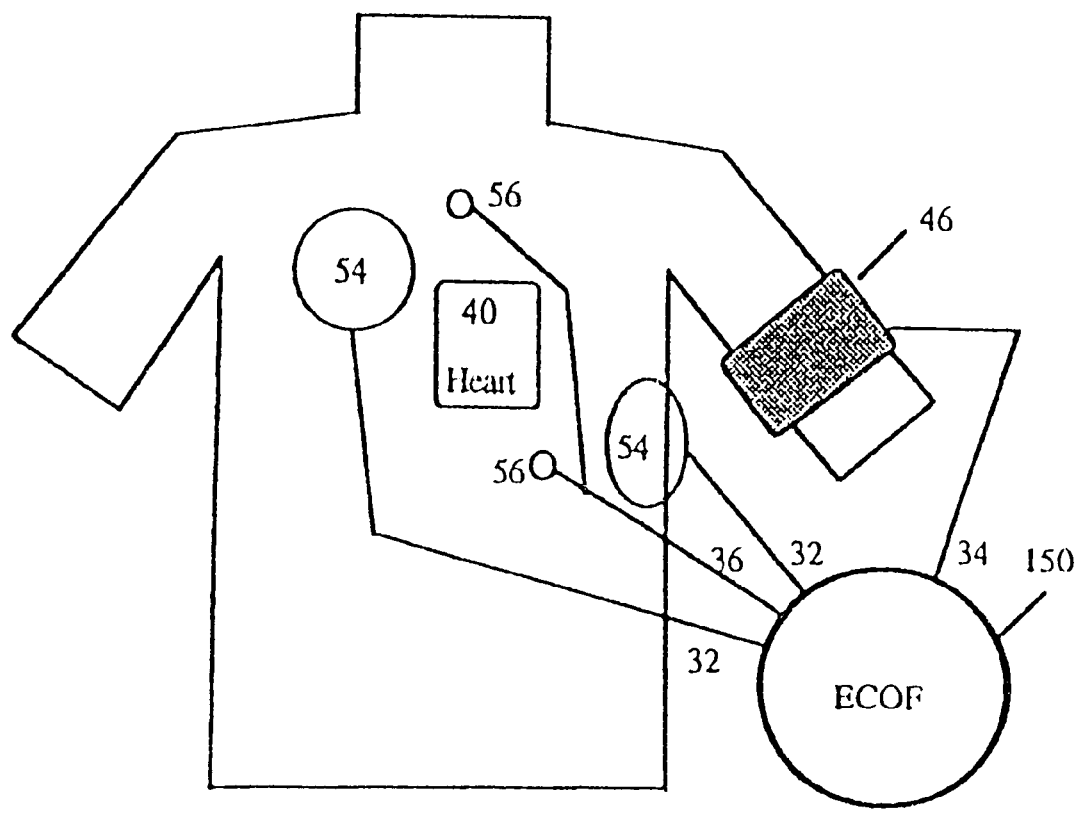
FIG. 3 shows the connection of an external embodiment of the invention.

FIG. 3 shows an external embodiment of the invention. External patch electrodes 54 are placed on the chest to deliver current to the heart 40 through output lead 32. The ECG is monitored by surface electrodes 56 and passed to the device 150 by a lead 36. Alternately, the ECG could be monitored by the external patch electrodes 54. An optional pressure sensor 46 passes a pressure signal via an optional pressure sense lead 34. This embodiment could be used as a substitute (due to its small size) for an external defibrillator and keep a patient alive until arrival at a hospital. Also, the system could precede the external defibrillator by generating output in patients in asystole until blood flow and rhythm are restored.

Figure 4:
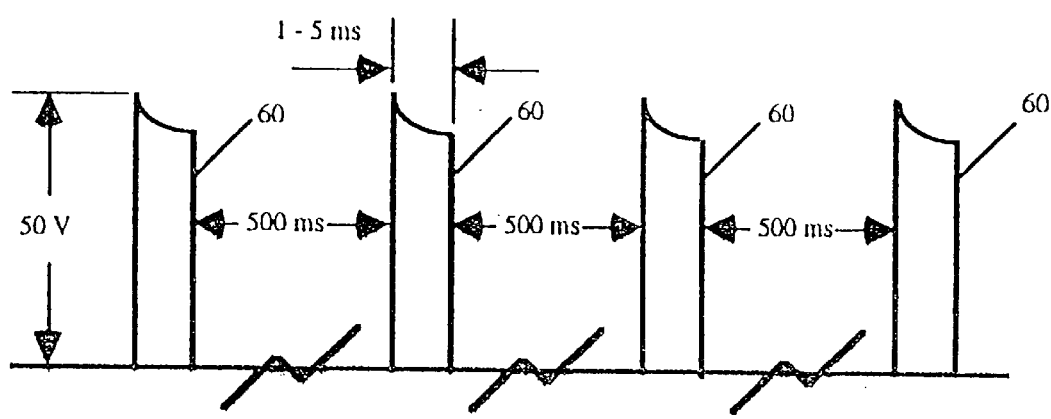
FIG. 4 is a diagram showing a representative pulsatile electrical signal.

A series of forcing pulses 60 are shown in FIG. 4. The pulses are approximately 50 V in amplitude with a spacing of approximately 500 ms. The 50 V and the 500 ms pulse spacing are chosen as illustrative for an implantable embodiment. The forcing pulse interval is chosen to maximize cardiac output within the limits of device circuitry and the response of the heart muscle. An interval of 500 ms corresponds to a heart rate of 120 beats per minute. This will produce a greater output than a typical resting rate of 60 beats per minute. However, a rate of 240 beats per minute would produce a lower output due to mechanical limitations of the heart. Thus a practical range is 60 to 200 beats per minute is appropriate. The pulses could also be timed to coincide with the natural pumping of the atria, thus improving overall cardiac output.

The higher the voltage, the higher the forcing fields, and therefore a greater number of heart cells contracting producing greater cardiac output. However, the higher voltage produces greater patient discomfort and extraneous muscle twitching.

Implantable batteries are also limited to a certain power output and energy storage. If an output pulse is 50 V and the electrode impedance is 50 Ω, the power during the pulse is $P = V^2/R = 50\ V * 50\ V/50\ \Omega = 50\ W$. If the pulse has a duration of 2 ms then the energy per pulse is 0.1 J. If two pulses are delivered every second, the charger must be capable of delivering 0.2 J per second which is 200 mW. This is well within the limits of an implantable battery. An implantable battery can typically deliver 5 W of power. However, 200 V pulses at 3 per second would require 4.8 W which is near the limit of the battery and charging circuitry. A typical implantable battery energy capacity is 10,000 J. Delivering forcing pulses at a rate of 4.8 W would deplete the battery in only 35 minutes (10,000 J/4.8 W=2083 seconds). Thirty five minutes may not be enough time to transport the patient to a hospital. Therefore 200 V represents the highest practical voltage for continuous operation in an implantable embodiment, although voltages of up to 350 V could be used for short periods and adjusted down when hemodynamic output is verified. A practical lower limit is about 10 V. During normal sinus rhythm, 10 V delivered through the patches would pace. However, during fibrillation the 10 V could not pace and only cells very near the electrodes would be captured. This would be insufficient for forcing cardiac output.

These calculations also suggest other differences between an implantable ECOF and an ICD. With a battery storing 10,000 J and an ECOF pulse having 0.1 J, this ECOF would be capable of delivering 100,000 pulses. An ICD can only deliver 200–400 shocks of about 30 J. The ECOF is also very different from an implantable pacemaker which typically delivers 150,000,000 pacing pulses (5 years at 60 BPM) each of about 0.00005 J.

For an external ECOF the calculations are similar, but scaled up. The typical ECOF pulse would have a voltage of 100 V with a range of 25–500 V. With electrode impedances of 50 Ω the power during the pulse is $P=V^2/R=100$ V*100 V/50 Ω=200 W with a range of 12.5–5,000 W. If the pulse has a duration of 2–5 ms, then the energy per pulse is 0.02–25 J. This is much less than the American Heart Association recommended output of 360 J for an external defibrillator.

This is also different from an external transthoracic pacemaker. These devices are rated by current and typically have an output range of 30–140 mA. Most patients are paced by pulses of 40–70 mA of current. An example of a modern external external thoracic pacemaker is given by Freeman in application WO 93/01861. Assuming an electrical impedance of 50 Ω and the ECOF voltage range of 25–500 V, then the ECOF current range would be 500 mA to 10 A. Since electrode impedance increases with lower voltage, the 25 V ECOF pulse would probably see an impedance of 100 Ω thereby giving a lower current of 250 mA.

Figure 5:
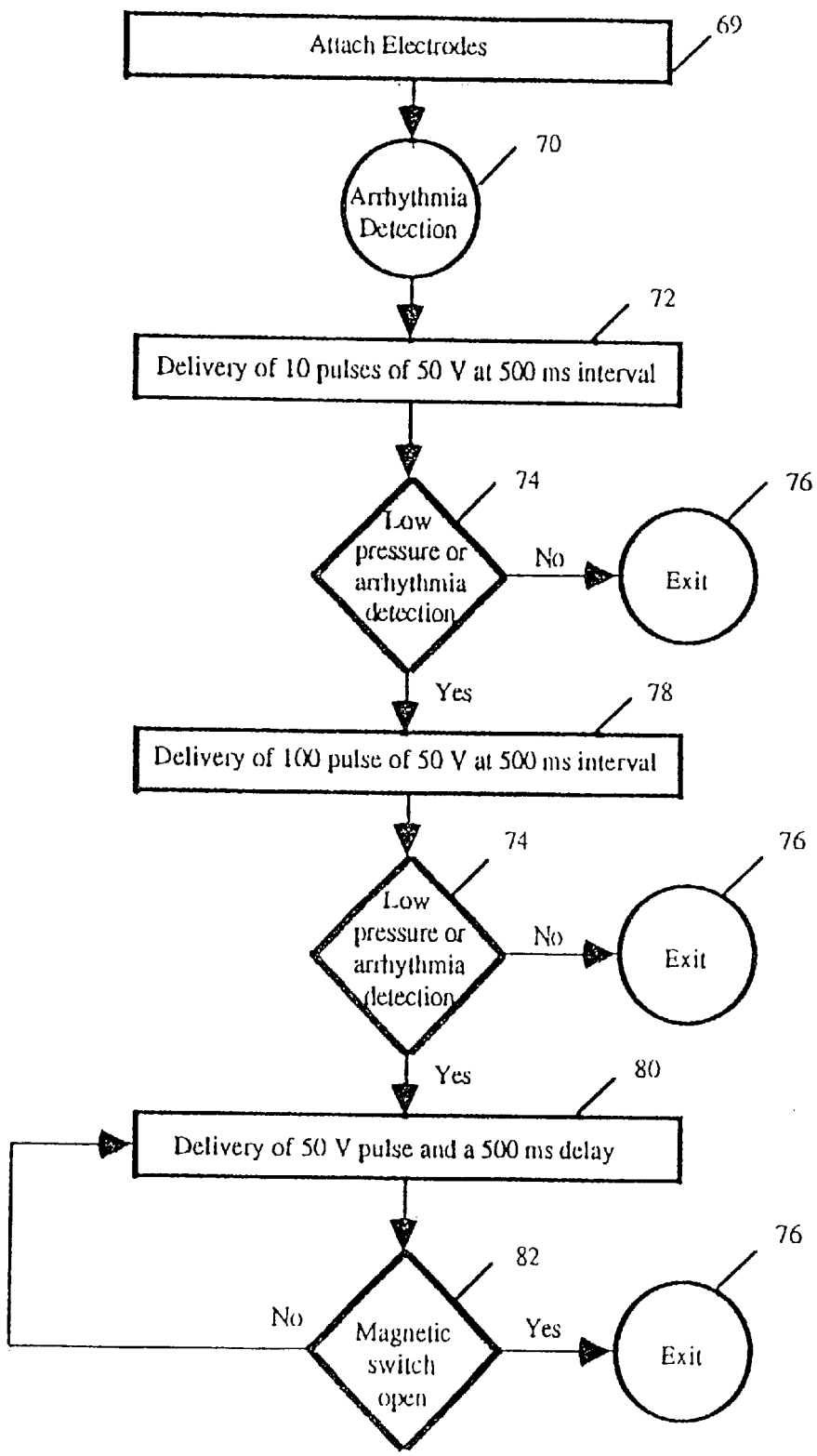
FIG. 5 is a flowchart illustrating one embodiment of the method of the invention.

FIG. 5 is a flowchart illustrating the method of the invention, which is provided for purposes of illustration only. One skilled in the art will recognize from the discussion that alternative embodiments may be employed without departing from the principles of the invention. The flow diagram shown in FIG. 5 represents a method of automatically treating a heart which is in fibrillation, tachycardia, or asystole and thereby pumping inefficiently or not at all. Electrodes are attached 69 and diagnoses the presence of an arrhythmia 70. A series of cardiac output forcing electric pulses 72 is automatically delivered. It should be understood that the therapy 72 may be delivered for any output compromising cardiac arrhythmia. After delivery of 10 forcing pulses (at a rate of 60–200 BPM) in the first block 72, the status of the heart is determined 74. If an arrhythmia is still present and there exists low pressure within the heart, more forcing pulses are delivered 78. If the heart is pumping at a safe level, the therapy ceases and exits 76. Note that this means that the ECOF successfully defibrillated the patient's heart even though this is not a primary goal of the system.

This could be tested in patients who were scheduled to receive an ICD, in a hospital setting. Those patients who are defibrillated by ECOF pulse therapy could then receive the ECOF instead of the larger ICD. After the therapy 78 has been delivered, the pressure and ECG is again monitored 74. If the therapy 78 is successful, it ceases and exits 76. If the therapy 78 is unsuccessful in producing a safe level of pumping efficiency, the method proceeds to a continuous cardiac assist mode 80. The therapy may only be stopped by an external command, for example, a telemetry signal or a magnet which is applied to the chest activating a magnetic reed switch 82 which terminates the therapy and exits 76. To minimize patient discomfort and maximize battery life, the forcing voltage could be adjusted down when sufficient pressure signals or adequate flow measured by other means were detected, for example, the pressure sense transducer could be replaced by an oxygen detector or a doppler flow measuring device. The pulse rate could also be adjusted to maximize output.

Figure 6:
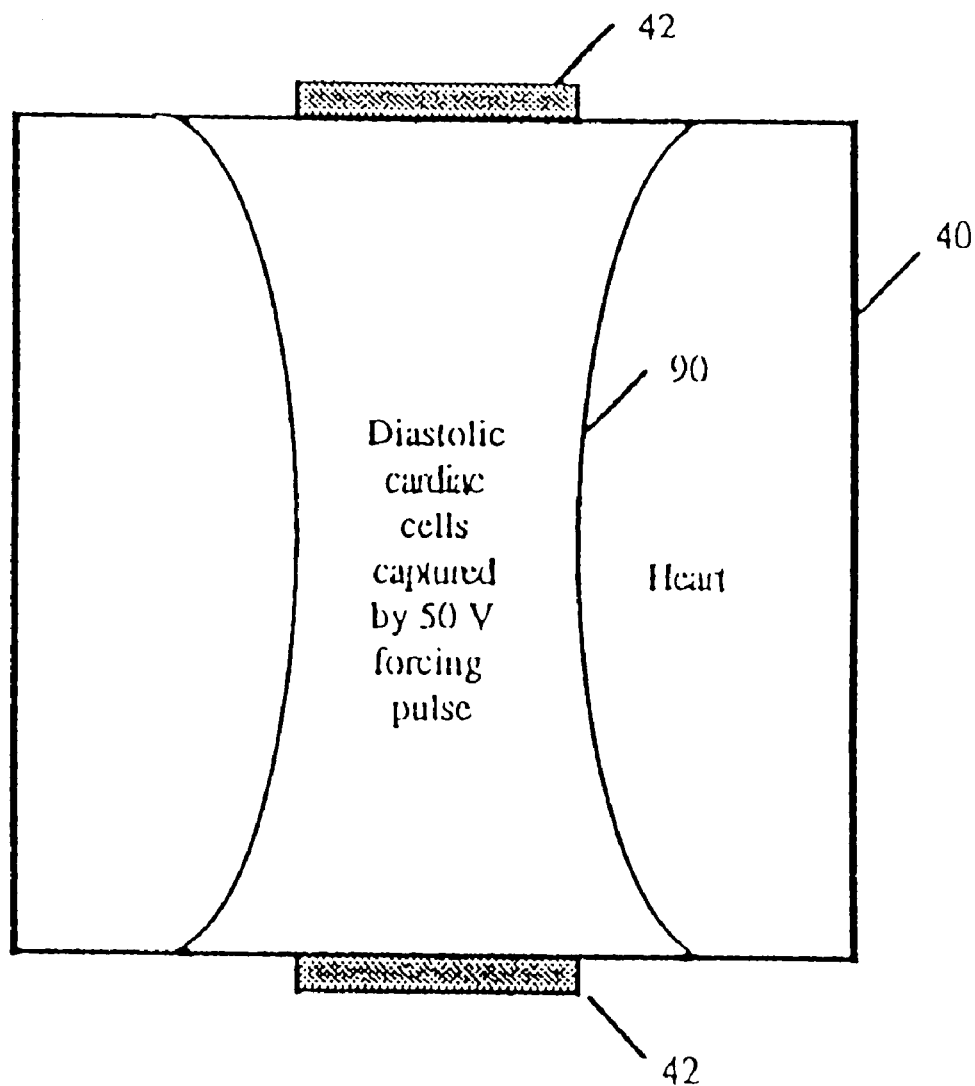
FIG. 6 is a diagram showing the expected effect of a 50 V pulse on the heart during diastole.

FIG. 6 is a diagram showing the effect of a 50 V forcing pulse on the heart 40 during electrical diastole (cells at rest). The current is passed through the heart 40 by the electrodes 42. Approximately 60% of cardiac cells 90 would be captured by a 50 V pulse if the cells were in diastole. The captured cells 90 mostly lie in the direct path between the electrodes 42 and near the electrodes 42 where the field strengths are highest. Of course, over a time period of about 100 ms these directly captured cells then propagate an activation wavefront to stimulate the rest of the heart. This so called far-field pacing is irrelevant here as the hearts, of interest, are in fibrillation and not in diastole.

Figure 7:
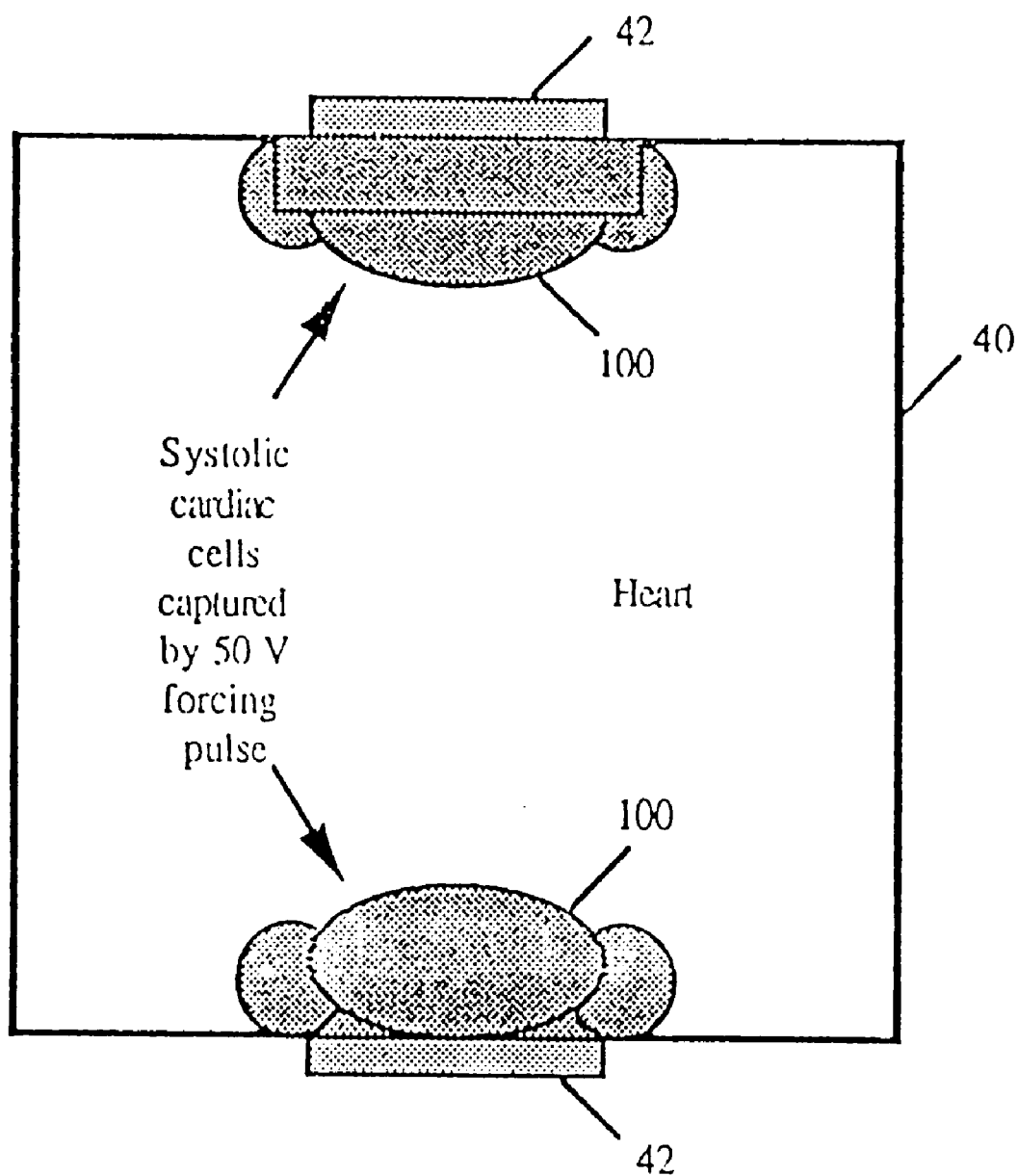
FIG. 7 is a diagram showing the expected effect of a 50 V pulse on the heart during systole.

FIG. 7 is a diagram showing the effect of a 50 V forcing pulse on the heart during electrical systole (cells already stimulated). The current is passed through the heart 40 by the electrodes 42. Approximately 20% of cardiac cells 100 would be captured by a 50 V pulse if the cells were in systole. The captured cells 100 are nearest each electrode 42 where the field strengths are highest. Capture in systolic cells means that their activation potential is extended. This capture requires significantly higher fields (10 V/cm) than those required for diastolic cell capture (1 V/cm).

Figure 8:
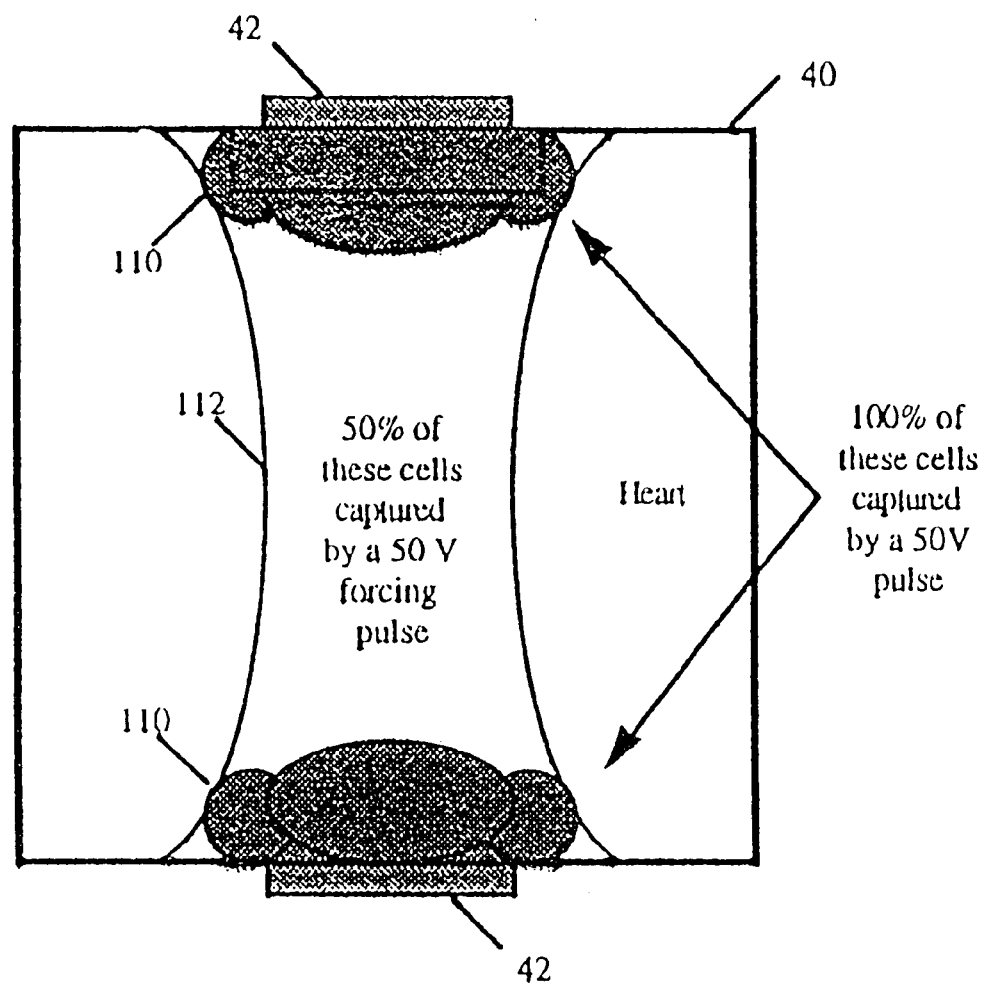
FIG. 8 is a diagram showing the expected effect of a 50 V pulse on the heart during fibrillation.

FIG. 8 is a diagram showing the effect of a 50 V forcing pulse on the heart during fibrillation. During fibrillation there are always cells in systole and diastole simultaneously. But, the vast majority are in systole. This diagram assumes 50% of the cells are in diastole which applies only after several capturing pulses. The current is passed through the heart 40 by the electrodes 42. 100% of the cells 110 nearest the electrodes 42 would be captured due to the high field strength. As shown in FIG. 7, even systolic cells are captured by high field strengths. 50% of the cells 112 in the direct path between the electrodes 42 would be captured if it is assumed that 50% of all cells are in diastole. If roughly 60% of cardiac cells are captured by a 50 V pulse when the cells are in diastole, and 20% are captured when in systole, and if 50% are in systole and 50% in diastole, 40% would be captured during fibrillation. This calculation is shown in the following table. The last two columns give the mechanical action resulting and the contribution to forcing a cardiac output.

Considering the cardiac cells that are originally in diastole, (rows A & B) in the table below, the A row represents the diastolic cells that are not captured by the forcing pulse. If 50% of the heart's cells are in diastole and 40% of those are not captured that is 20% of the total cells. These cells will, however, shortly contract on their own (from previous wavefronts or new ones) providing a positive gain in mechanical action and therefore cardiac output. The B row corresponds to the diastolic cells that are captured. If 60% of the diastolic cells (50% of total) contract due to the forcing field this is 30% of the total heart cells. These cells provide the biggest gain in mechanical action and cardiac output. Next considering the activity of the systolic cells (rows C & D), if 50% of the heart's cells are in systole and 80% of those are not captured (row C), that is 40% of the heart's cells. These cells soon relax and negate a portion of the cardiac output. The systolic cells that are captured (row D) are 10% of the heart's cells (20% of 50%). These cells will hold their contraction and be neutral to cardiac output. The net result is a gain in contraction which forces cardiac output.

Figure 9A:
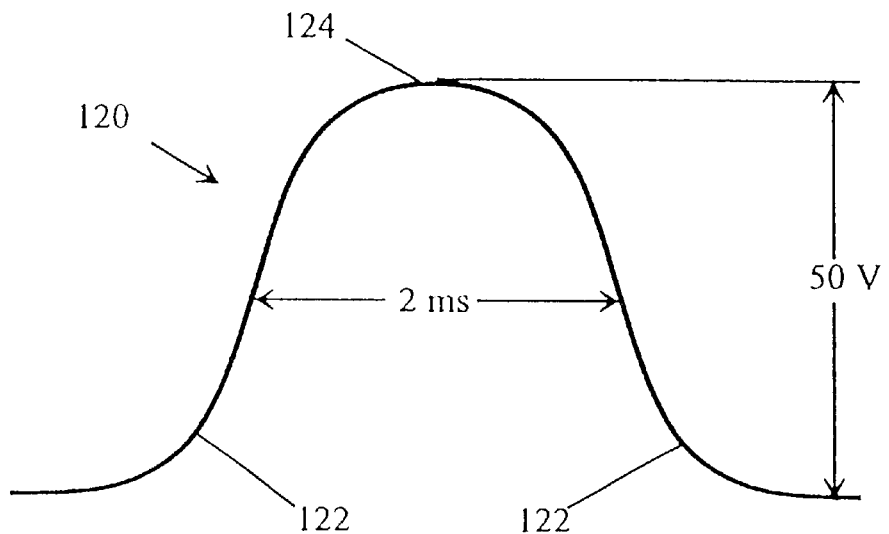
FIGS. 9a and 9b show various waveforms useful for the electrical cardiac output forcing method and apparatus.
Figure 9B:
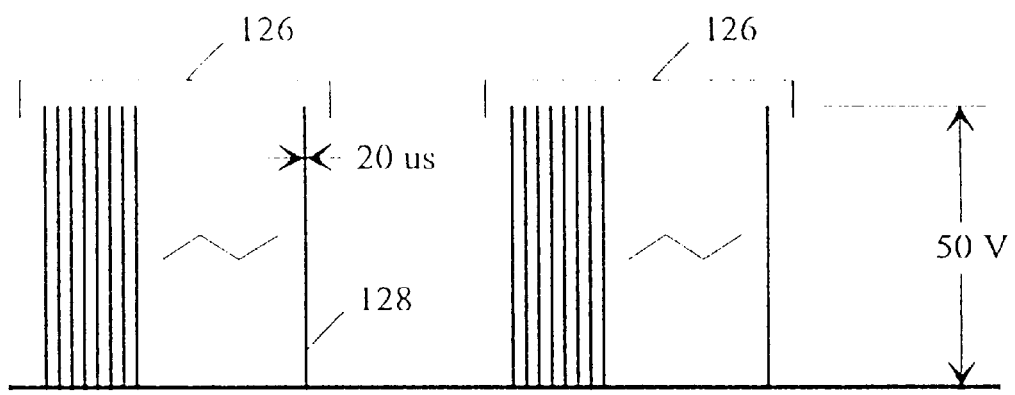

FIG. 9b shows a technique of going to the opposite extreme. Here, each compound forcing pulse 126 is actually composed of 50 very short spikes 128 each of which is 20 $\mu$s in width with a 20 $\mu$s spacing. The heart will tend to average out these thin pulses and "see" a 2 ms wide forcing pulse. The skeletal muscle, however, is not efficiently stimulated by these extremely narrow pulses. The skeletal muscle will not average out this signal either. This approach could help minimize skeletal muscle twitching and discomfort.

An alternative system would be to charge the capacitor to 300 V for the first pulse to capture many cells therefore putting those cells into diastole after a delay of 100–200 ms. At this point the voltage could be lowered to 100 V and delivered every 100 ms. A 3 watt DC-DC converter with a

| Original status of the cells | Percentage of the cardiac cells | Status of the cardiac cells | Percentage of the original status | Percentage of the total cells | Mechanical Action | Forcing Cardiac Output Effect |
|---|---|---|---|---|---|---|
| (A) Diastolic | 50% | Diastolic non-captured | 40% of 50% | 20% | will start to contract on own | positive (+) |
| (B) Diastolic | | Diastolic captured | 60% of 50% | 30% | contract | positive (++) |
| (C) Systolic | 50% | Systolic non-captured | 80% of 50% | 40% | will start to relax on own | negative (−) |
| (D) Systolic | | Systolic captured | 20% of 50% | 10% | hold | neutral (0) |
| Total | 100% | | 100% | 100% | more contraction | positive (++) |

The net result over a 200 ms mechanical response is given in the next table. The major contribution is in row (B) from the captured diastolic cells contracting.

| Row | Status of the Cardiac Cells | Change in Output | Description of Activity |
|---|---|---|---|
| A | Diastolic non-captured | +5% | Positive. Some cells will begin to contract on their own. |
| B | Diastolic captured | +30% | Positive. Cells contract due to forcing field. |
| C | Systolic non-captured | −5% | Negative. Some cells will begin to relax on their own. |
| D | Systolic captured | 0% | Neutral. Cells hold contraction due to forcing field. |
| Net Gain | | +30% | A net gain in cardiac output due to forcing fields. |

The 30% net pumping action should be sufficient to maintain survival and consciousness, because the heart has a 4–5 times reserve capacity.

FIG. 9 depicts examples of waveforms designed to minimize the twitching of the chest muscles which can be very uncomfortable to the patient. In FIG. 9a is seen a low harmonic pulse waveform 120 which has a very gradual "foot" 122 and a gradual peak 124. Such a pulse has less high frequency energy components and thus is less likely to stimulate the skeletal muscle.

67% efficiency could provide 100 ms interval forcing pulses assuming a 50 $\Omega$ resistance and 1 ms pulse (0.2 J). This rate is too fast for forcing cardiac output due to mechanical limitations, but is very effective for electrical capture. After sufficient capture, the rate of forcing pulses could be slowed down to 100–170 beats per minute for optimum cardiac output.

The Electrical Cardiac Output Forcing device (ECOF) could also be used to help patients with atrial fibrillation. As an alternative embodiment to the ventricular placement of FIG. 2b, the electrode coil 52 and sensing electrodes 44 could be placed in the atrium. The device could then function to force atrial output. Even though atrial fibrillation is not instantly fatal like ventricular fibrillation is, clots can build up in the atria which can eventually lead to strokes. Cardiac output forcing of the atria on a daily basis may limit this problem. It is also possible that after a number of forcing pulses the atria would return to a normal rhythm. There is however, no urgency as is the case with ventricular fibrillation.

Figure 10:
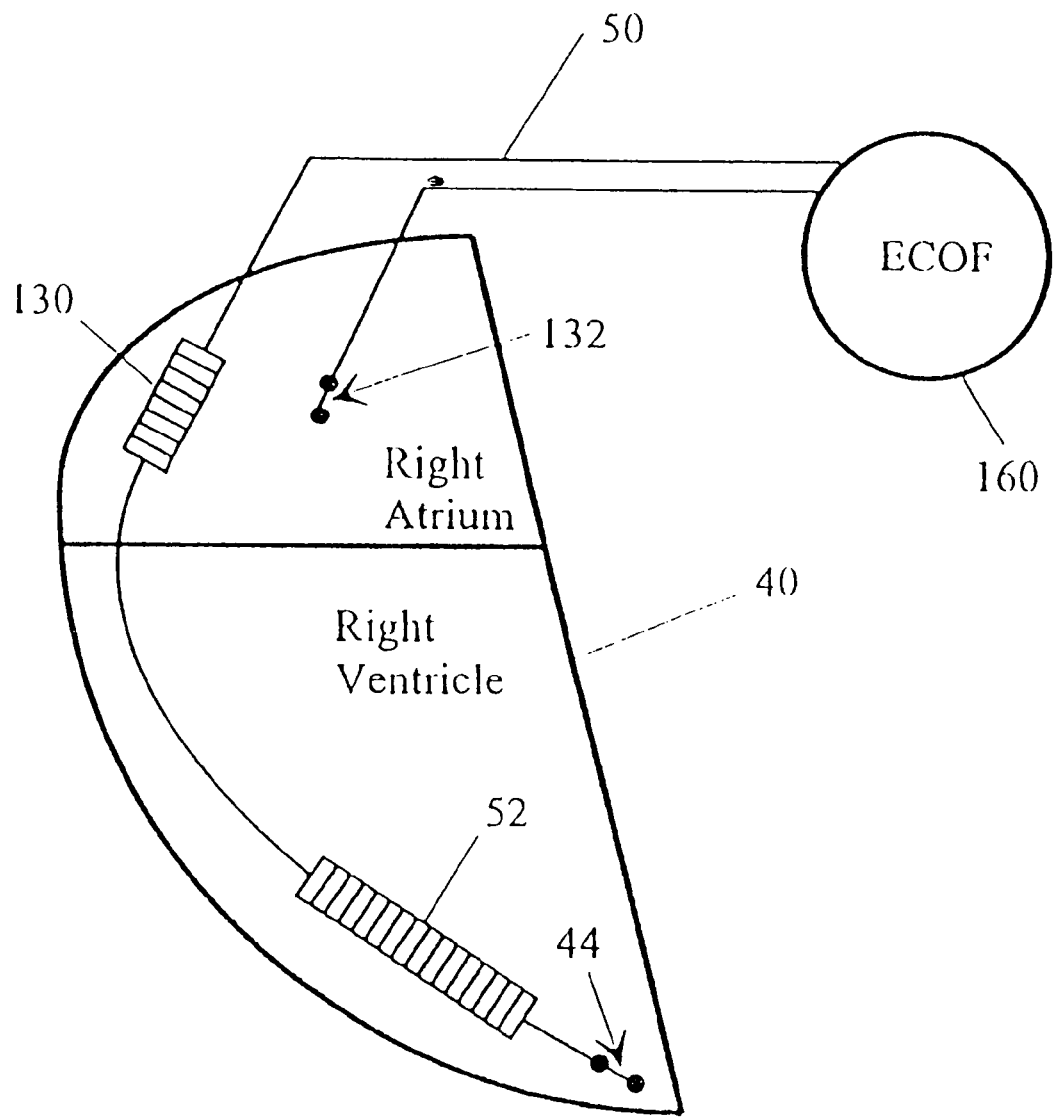
FIG. 10 shows the device used as a backup to an atrial defibrillator.

A second use of this invention for atrial defibrillation is shown in FIG. 10. As before in FIG. 2b, the ECOF 160 is shown connected to the heart 40 via endocardial lead 50. Again forcing coil electrode 52 and sensing electrodes 44 are in the right ventricle. In addition a large atrial coil electrode 130 and atrial sensing electrodes 132 are in the right atrium. These would be used for conventional atrial defibrillation. One of the big concerns with atrial defibrillation is that in a few cases, an atrial defibrillation shock causes ventricular fibrillation. If this happens, the patient dies within minutes. With the ECOF approach, for the left ventricle, one could maintain output in the patient for several hours and thus have enough time for transport to a hospital or external defibrillation. Thus the ECOF approach in the ventricle could provide a safety backup to atrial defibrillation.

Many cardiac patients have no known risk of ventricular fibrillation, but suffer regularly from ventricular tachycardia. Accordingly, these people can be treated with anti-tachycardia pacing (ATP). Unfortunately, occasionally ATP will cause a ventricular fibrillation. Then a large defibrillation shock must be applied. Thus it is not considered safe to implant a pure ATP device and these patients instead receive a full size ICD. The ECOF approach also serves as a safety backup and thus allow the implantation of true ATP devices. The system is depicted in FIG. 2b, although the pressure sensor 46 would typically not be needed.

Low energy cardioverters can also be used to treat ventricular tachycardias. These devices are also not considered safe as stand alone devices due to the fact that they may not terminate the rhythm or that they may cause fibrillation. The ECOF method also could is used as a safety backup thus allowing the implantation of cardioverters without defibrillation capabilities. Such a system is shown in FIG. 2b.

It should be understood that various alternatives to the embodiments of the invention described herein may be employed in practicing the invention. For example, while most of the discussion is in the context of an implantable device, the concepts of the invention are also applicable to external delivery systems. It is intended that the following claims define the scope of the invention and that structures and methods within the scope of these claims and their equivalents be covered thereby.

We claim:

1. A method for forcing cardiac output during tachyarrhythmia in a patient, comprising the steps of:
    (a) attaching a plurality of electrodes to external portions of a patient's body proximate the patient's thoracic region so that the electrodes may deliver electrical pulses which will be transmitted through portions of the patient's upper body;
    (b) providing means for detecting the presence of tachyarrhythmia in the patient;
    (c) detecting the presence of tachyarrhythmia in the patient;
    (d) delivering electrical current pulses through the patient's body, via said electrodes after detecting tachyarrhythmia, at a rate between about 60 and 200 pulses per minute, said electrical current pulses having a voltage less than a normal defibrillation voltage level, to force contraction in the patient's heart and facilitate a minimum level of cardiac output until cessation of the tachyarrhythmia or until other medical intervention is provided; and
    (e) delivering further medical intervention if the desired minimum level of cardiac output has not occurred, said medical intervention comprising delivering at lease one external defibrillation pulse to the patient following a plurality of said electrical current pulses.

2. The method of claim 1, further comprising the steps of reassessing the presence of an arrhythmia at predetermined intervals and terminating said delivery of electrical current pulses or defibrillation pulses if the arrhythmia is no longer present.

3. The method of claim 1, in which each electrical current pulse has an energy of less than about 360 joules.

4. The method of claim 1, further comprising the steps of monitoring cardiac output and adjusting said electrical current pulse with respect to amplitude to maintain a predetermined level of cardiac output, thereby conserving electrical energy.

5. The method of claim 1, wherein a plurality of said electrical current pulses have rounded edges.

6. The method of claim 1 further comprising the step of forming a plurality of said electrical current pulses as a train of at least about 10 narrow pulses.

7. The method of claim 1, wherein said step of delivering electrical current pulses is repeated for at least thirty minutes to maintain some cardiac output.

8. The method of claim 1, wherein the step of delivering electrical current pulses comprises delivery of a plurality of pulses which are greater than about 250 mA.

9. The method of claim 1, wherein said step of delivering electrical current pulses is performed immediately after detecting tachyarrythmia.

10. A method for producing minimal cardiac output on an emergency basis in a patient experiencing arrhythmia, comprising the steps of:
    (a) attaching a plurality of electrodes to external portions of a patient's chest so that the electrodes may deliver electrical pulses which will be transmitted through portions of the patient's upper body;
    (b) providing means for detecting the presence of arrhythmia in the patient;
    (c) detecting the presence of arrhythmia in the patient;
    (d) delivering a defibrillation pulse to an external portion of the patient's body; and
    (e) delivering electrical current pulses through the patient's body, via said electrodes after said defibrillation pulse delivery and after detecting arrhythmia, at a rate between about 60 and 200 pulses per minute, said electrical current pulses having a voltage greater than that which would only pace the heart and less than that which would defibrillate the patient's heart, so as to force some contraction in the patient's heart, whereby a minimum level of cardiac output is maintained until cessation of the arrhythmia or until other medical intervention is provided.

11. The method of claim 10, in which the power supply means provides electrical current pulses through the electrodes in a voltage range of greater than about 25 volts and less than about 2000 volts.

12. The method of claim 10, in which the arrythmia includes either tachycardia or bradycardia.

13. The method of claim 10, further comprising the step of electronically interfacing said means for detecting the presence of arrythmia in the patient with said other medical intervention.

14. The method of claim 10, wherein the step of delivering electrical current pulses comprises delivery of a plurality of pulses which are greater than about 250 mA.

15. A system, for external use on a human body, for maintaining some cardiac output of a patient's heart during arrhythmia using electrical forcing fields, comprising:
    (a) power supply means;
    (b) arrhythmia detection means connected to said power supply means;
    (c) pulse delivery means connected to said power supply means for delivering multiple electrical current pulses through portions of the patient's upper body;
    (d) output control means connected to said arrhythmia detection means, said power supply means, and said pulse delivery means for controlling the delivery of multiple electrical current pulses to the patient's upper body after the detection of arrhythmia, said electrical current pulses having a voltage greater than about 25 volts and less than the voltage necessary to defibrillate the patient, said output control means providing pulses suitable for only producing contraction in the patient's heart sufficient to maintain a level of cardiac output which is a fraction of the normal maximum cardiac output until cessation of the arrhythmia or until other medical intervention is provided; and (e) external defibrillation means cooperating with said output control means and adapted for delivering at least one external defibrillation pulse to the patient's body when said contraction in the patient's heart is not sufficient to maintain a desired level of cardiac output and when said pulse delivery means is not delivering said electrical current pulses.

16. The system of claim 15, in which said electrical current pulses are delivered at a rate between about 60 and 200 beats per minute.

17. The system of claim 15, further comprising cardiac output sensing means.

18. The system of claim 15, further comprising cardiac pressure sensing means.

19. The system of claim 15, further comprising blood pressure monitoring means connected to said arrhythmia detection means.

20. The system of claim 15, further comprising doppler sensing means for monitoring cardiac output, said doppler sensing means functionally operable with said arrhythmia detection means.

21. The system of claim 15, in which said blood pressure monitoring means monitors cardiac output and further comprises means for adjusting said electrical current pulse amplitude by said output control means to maintain an optimum therapy for maintaining cardiac output.

22. The system of claim 15, wherein a plurality of said electrical current pulses have rounded edges.

23. The system of claim 15, further comprising the step of providing means for forming a plurality of said electrical current pulses as a train of at least 10 narrow pulses.

24. The system of claim 15, in which said arrythmia detection means comprises means for reassessing the presence of arrhythmia at predetermined intervals and stopping said electrical current pulses with said output control means if the arrhythmia is no longer present.

25. The system of claim 15, in which said arrythmia detection means comprises means for reassessing the presence of arrhythmia and cardiac output at predetermined intervals and adjusting said electrical current pulses with said output control means according to said reassessment.

26. The system of claim 15, in which said power supply means and said output control means deliver said electrical current pulses at a level to maintain cardiac output for at least about 30 minutes.

27. The system of claim 15, wherein said output control means comprises means for delivering said electrical current pulses for at least one hour to maintain cardiac output.

28. The system of claim 15, in which additional heart treatment devices are used in combination therewith including means to perform conventional anti-tachycardia pacing, means to perform tachycardia cardioversion, or means to perform various forms of defibrillation.

29. The system of claim 15, in which the power supply means, the output control means, and the arrhythmia detection means operate to produce a cardiac output of between about 10% and about 90% of the normal maximum cardiac output for the patient.

30. The system of claim 15, in which the power supply means, the output control means, and the arrhythmia detection means operate to produce a cardiac output of between about 20% and about 80% of the normal maximum cardiac output for the patient.

31. The system of claim 15, in which the power supply means, the output control means, and the arrhythmia detection means operate to produce a cardiac output of greater than about 30% of the normal maximum cardiac output for the patient.

32. The system of claim 15, wherein the electrical current pulses are greater than about 250 mA.

33. A device, for external attachment to a human body, for maintaining some cardiac output of a patient's heart during dysrhythmia using electrical forcing fields, comprising:

(a) power supply means for providing power to pulse delivery means, arrythmia detection means, and output control means;

(b) arrhythmia detection means operatively connected to said power supply means;

(c) first pulse delivery means operatively connected to said power supply means for delivering multiple electrical current pulses through portions of the patient's upper body, said multiple electrical pulses comprising cardiac therapy responsive to the particular patient's cardiac rhythm;

(d) output control means operatively connected to said arrhythmia detection means, said power supply means, and said first pulse delivery means for controlling the delivery of multiple electrical current pulses to the human heart after the detection of arrhythmia; said electrical current pulses having an amplitude suitable for delivery through the patient's upper body and for contributing to the mechanical and electrical mechanisms adequate to produce contractions in the patient's heart and to cause only a fraction of the normal maximum cardiac output but enough cardiac output to maintain cardiac viability until cessation of the dysrhythmia or until other medical intervention is provided; and (e) second pulse delivery means operably interfaced with at least said output control means for delivering at least one external defibrillation pulse to the patient's body when further medical intervention is required.

34. The device of claim 33 in which the amplitude of the electrical current pulses is greater than a cardiac pacing level of about 20 volts and less than a normal cardiac defibrillating voltage of about 2000 volts.

35. The device of claim 33, in which said electrical current pulses comprise pulses which are greater than about 140 mA.

36. The device of claim 33, in which said electrical current pulses comprise pulses which are less than about 20 ms.

37. A method for providing hemodynamic output of a heart during arrythmia, comprising the steps of:

(a) attaching a plurality of electrodes to external portions of a patient's body proximate the patient's chest so that the electrodes may deliver or receive electrical pulses transmitted through portions of the patient's upper body;

(b) providing means for detecting the presence of arrhythmia in the patient;

(c) detecting the presence of arrhythmia in the patient;

(d) delivering a first series of electrical current pulses for a first period of time, through the patient's body, via said electrodes after detecting arrhythmia; said electrical current pulses having a voltage less than a normal defibrillation voltage level but enough to force hemodynamic activity by mechanical and electrical responses of the patient's body to facilitate contraction of the patient's heart and to facilitate a minimum level of cardiac output;

(e) determining the output status of the heart;

(f) if the output status of the heart requires, then delivering at least one electrical defibrillation pulse having a voltage level sufficient to defibrillate the patient's heart; and (g) determining the output status of the heart.

38. The method of claim 37, in which the step of determining the output status of the heart comprises detecting whether arrythmia still exists.

39. The method of claim 37, in which the step of determining the output status of the heart comprises detecting whether there is an abnormal low pressure within the heart.

40. The method of claim 37, further comprising the step of delivering at least one further series of electrical current pulses, after delivering said first electrical defibrillation pulse, and after determining the output status of the heart, and if said determination indicates a continued existence of arrythmia or the presence of a low pressure in the heart indicative of inadequate cardiac output.

41. The method of claim 37, in which the electrical current pulses are timed to coincide with the natural pumping of the patient's atria.

42. The method of claim 37, in which said step of determining the output status of the heart comprises initiation by said output control means of an adjustment of the characteristics of said electrical current pulses according to said determined output status.

43. A method for providing hemodynamic output of a heart during arrythmia, comprising the steps of:

(a) attaching a plurality of electrodes to external portions of a patient's body proximate the patient's chest so that the electrodes may deliver or receive electrical pulses transmitted through portions of the patient's upper body;

(b) providing means for detecting the presence of arrhythmia in the patient;

(c) detecting the presence of arrhythmia or low cardiac output in the patient;

(d) delivering a first series of electrical current pulses for a first period of time, through a portion of the patient's body, via electrodes after detecting said arrhythmia, said first series of electrical current pulses comprising at least one electrical current pulse having a voltage level suitable for defibrillating the patient's heart;

(e) delivering a second series of electrical current pulses for a first period of time, through a portion of the patient's body, via said electrodes after detecting arrhythmia; said second series of electrical current pulses comprising a plurality of pulses having a voltage level less than a normal defibrillation voltage level but enough to force hemodynamic activity by contraction of the patient's heart and to facilitate a minimum level of cardiac output.

44. The method of claim 43 further comprising the step of determining the output status of the heart.

45. The method of claim 43 in which the arrythmia is of an asystole type relating to absence of cardiac contraction and leading to cardiac arrest.

46. The method of claim 43, in which the pulse widths of said second series pulses are between about 1 ms and about 50 ms.

47. A method for conducting emergency electrical cardiac output in a human, comprising the steps of:

(a) attaching a plurality of electrodes to external portions of a patient's body so that the electrodes may deliver electrical pulses which will be transmitted through portions of the patient's upper body;

(b) providing means for detecting the presence of arrhythmia in the patient;

(c) detecting the presence of arrhythmia in the patient;

(d) delivering electrical current pulses through the patient's body to the patient's heart, via said electrodes after detecting arrhythmia, at a voltage level of less than a defibrillating voltage level, to force contraction in the patient's heart and to facilitate a minimum level of cardiac output until cessation of the arrhythmia or until other medical intervention is provided; and (e) providing further medical intervention by delivering a series of defibrillation pulses through the patient's body, said series comprising at least one electrical current pulse having a voltage level sufficient to defibrillate the patient's heart.

48. The method of claim 47 in which the electrical current pulses are delivered at a rate of less than about 200 pulses per minute.

49. A method for forcing cardiac output during tachyarrhythmia in a patient, comprising the steps of:

(a) positioning a plurality of electrodes proximate portions of a patient's heart so that the electrodes may deliver electrical pulses which will be transmitted through the patient's heart;

(b) providing means for detecting the presence of tachyarrhythmia in the patient;

(c) detecting the presence of tachyarrhythmia in the patient;

(d) delivering electrical current pulses through the patient's heart, via said electrodes after detecting tachyarrhythmia, said electrical current pulses having a voltage less than a normal defibrillation voltage level, to force contraction in the patient's heart and to facilitate a minimum level of cardiac output until cessation of the tachyarrhythmia or until other medical intervention is provided; and (e) delivering further medical intervention if the desired minimum level of cardiac output has not occurred, said medical intervention comprising delivering at lease one defibrillation pulse to the patient following a plurality of said electrical current pulses.

50. The method of claim 49, further comprising the steps of reassessing the presence of an arrhythmia at predetermined intervals and terminating said delivery of electrical current pulses or defibrillation pulses if the arrhythmia is no longer present.

51. The method of claim 49, in which each electrical current pulse has an energy of less than about 360 joules.

52. The method of claim 49, further comprising the steps of monitoring cardiac output and adjusting said electrical current pulse with respect to amplitude to maintain a predetermined level of cardiac output, thereby conserving electrical energy.

53. The method of claim 49, wherein a plurality of said electrical current pulses have rounded edges.

54. The method of claim 49, further comprising the step of forming a plurality of said electrical current pulses as a train of at least about 10 narrow pulses.

55. The method of claim 49, wherein said step of delivering electrical current pulses is repeated for at least thirty minutes to maintain some cardiac output.

56. The method of claim 49, wherein the step of delivering electrical current pulses comprises delivery of a plurality of pulses which are greater than about 250 mA.

57. The method of claim 49, wherein said step of delivering electrical current pulses is performed immediately after detecting tachyarrythmia.

58. The method of claim 49, wherein said defibrillation pulse is delivered to the patient internally.

59. A method for producing minimal cardiac output on an emergency basis in a patient experiencing arrhythmia, comprising the steps of:
  (a) positioning a plurality of electrodes to enable delivery of electrical pulses which will be transmitted through portions of the patient's upper body;
  (b) providing means for detecting the presence of arrhythmia in the patient;
  (c) detecting the presence of arrhythmia in the patient;
  (d) delivering a defibrillation pulse within the patient's body; and
  (e) delivering electrical current pulses through the patient's body, via said electrodes after said defibrillation pulse delivery and after detecting arrhythmia, said electrical current pulses having a voltage greater than that which would only pace the heart and less than that which would defibrillate the patient's heart, so as to force some contraction in the patient's heart, whereby a minimum level of cardiac output is maintained until cessation of the arrhythmia or until other medical intervention is provided.

60. The method of claim 59, in which the power supply means provides electrical current pulses through the electrodes in a voltage range of greater than about 25 volts and less than about 2000 volts.

61. The method of claim 59, in which the arrythmia includes either tachycardia, asystole, or bradycardia.

62. The method of claim 59, further comprising the step of electronically interfacing said means for detecting the presence of arrythmia in the patient with said other medical intervention.

63. The method of claim 59, wherein the step of delivering electrical current pulses comprises delivery of a plurality of pulses which are greater than about 250 mA.

64. An at least partially implantable system, for internal use on a human body, for maintaining some cardiac output of a patient's heart during arrhythmia using electrical forcing fields, comprising:
  (a) power supply means;
  (b) arrhythmia detection means connected to said power supply means;
  (c) pulse delivery means connected to said power supply means for delivering multiple electrical current pulses through portions of the patient's upper body;
  (d) output control means connected to said arrhythmia detection means, said power supply means, and said pulse delivery means for controlling the delivery of multiple electrical current pulses to the patient's upper body after the detection of arrhythmia, said electrical current pulses having a voltage level less than the voltage necessary to defibrillate the patient, said output control means providing pulses suitable for only producing contraction in the patient's heart sufficient to maintain a level of cardiac output which is a fraction of the normal maximum cardiac output until cessation of the arrhythmia or until other medical intervention is provided; and
  (e) internal defibrillation means cooperating with said output control means and adapted for delivering at least one internal defibrillation pulse to the patient's body when said contraction in the patient's heart is not sufficient to maintain a desired level of cardiac output and when said pulse delivery means is not delivering said electrical current pulses.

65. The system of claim 64, in which said electrical current pulses are delivered at a rate between about 60 and 200 beats per minute.

66. The system of claim 64, further comprising cardiac output sensing means.

67. The system of claim 64, further comprising cardiac pressure sensing means.

68. The system of claim 64, further comprising blood pressure monitoring means connected to said arrhythmia detection means.

69. The system of claim 64, further comprising doppler sensing means for monitoring cardiac output, said doppler sensing means functionally operable with said arrhythmia detection means.

70. The system of claim 64, in which said blood pressure monitoring means monitors cardiac output and further comprises means for adjusting said electrical current pulse amplitude by said output control means to maintain an optimum therapy for maintaining cardiac output.

71. The system of claim 64, wherein a plurality of said electrical current pulses have rounded edges.

72. The system of claim 64, further comprising the step of providing means for forming a plurality of said electrical current pulses as a train of at least 10 narrow pulses.

73. The system of claim 64, in which said arrythmia detection means comprises means for reassessing the presence of arrhythmia at predetermined intervals and stopping said electrical current pulses with said output control means if the arrhythmia is no longer present.

74. The system of claim 64, in which said arrythmia detection means comprises means for reassessing the presence of arrhythmia and cardiac output at predetermined intervals and adjusting said electrical current pulses with said output control means according to said reassessment.

75. The system of claim 64, in which said power supply means and said output control means deliver said electrical current pulses at a level to maintain cardiac output for at least about 30 minutes.

76. The system of claim 64, wherein said output control means comprises means for delivering said electrical current pulses for at least one hour to maintain cardiac output.

77. The system of claim 64, in which the power supply means, the output control means, and the arrhythmia detection means operate to produce a cardiac output of between about 10% and about 90% of the normal maximum cardiac output for the patient.

78. The system of claim 64, in which the power supply means, the output control means, and the arrhythmia detection means operate to produce a cardiac output of between about 20% and about 80% of the normal maximum cardiac output for the patient.

79. The system of claim 64, in which the power supply means, the output control means, and the arrhythmia detection means operate to produce a cardiac output of greater than about 30% of the normal maximum cardiac output for the patient.

80. The system of claim 64, wherein the electrical current pulses are greater than about 250 mA.

81. An implantable device for maintaining some cardiac output of a patient's heart during dysrhythmia using electrical forcing fields, comprising:
  (a) power supply means for providing power to pulse delivery means, arrythmia detection means, and output control means;

(b) arrhythmia detection means operatively connected to said power supply means;

(c) first pulse delivery means operatively connected to said power supply means for delivering multiple electrical current pulses through portions of the patient's upper body, said multiple electrical pulses comprising cardiac therapy responsive to the particular patient's cardiac rhythm;

(d) output control means operatively connected to said arrhythmia detection means, said power supply means, and said first pulse delivery means for controlling the delivery of multiple electrical current pulses to the human heart after the detection of arrhythmia; said electrical current pulses having an amplitude suitable for delivery through portions of the patient's upper body and for contributing to the mechanisms that produce contractions in the patient's heart which to cause only a fraction of the normal maximum cardiac output but enough cardiac output to maintain cardiac viability until cessation of the dysrhythmia or until other medical intervention is provided; and (e) second pulse delivery means operably interfaced with at least said output control means for delivering at least one defibrillation pulse to the patient's body when further medical intervention is required.

82. The device of claim 81 in which the amplitude of the electrical current pulses is greater than a cardiac pacing level of about 20 volts and less than a cardiac defibrillating voltage.

83. The device of claim 81 in which the voltage is less than about 2000 volts.

84. The device of claim 81 in which the voltage is less than about 1000 volts.

85. The device of claim 81 in which the voltage is less than about 500 volts.

86. The device of claim 81, in which said electrical current pulses comprise pulses which are greater than about 140 mA.

87. The device of claim 81, in which said electrical current pulses comprise pulses which are less than about 20 ms.

88. The device of claim 81 in which said second pulse delivery means is an implantable cardioverter defibrillator.

89. A method for providing hemodynamic output of a heart during arrythmia, comprising the steps of:

(a) positioning a plurality of electrodes in a patient's body proximate the patient's heart so that the electrodes may deliver or receive electrical pulses transmitted through portions of the patient's upper body and heart;

(b) providing means for detecting the presence of arrhythmia in the patient;

(c) detecting the presence of arrhythmia in the patient;

(d) delivering a first series of electrical current pulses for a first period of time via said electrodes after detecting arrhythmia; said electrical current pulses having a voltage less than a normal defibrillation voltage level but enough to force hemodynamic activity by mechanical and electrical responses of the patient's body to facilitate contraction of the patient's heart and to facilitate a minimum level of cardiac output;

(e) determining the output status of the heart;

(f) if the output status of the heart requires, then delivering at least one electrical defibrillation pulse having a voltage level sufficient to defibrillate the patient's heart; and (g) determining the output status of the heart.

90. The method of claim 89, in which the step of determining the output status of the heart comprises detecting whether arrhythmia still exists.

91. The method of claim 89, in which the step of determining the output status of the heart comprises detecting whether there is an abnormal low pressure within the heart.

92. The method of claim 90, further comprising the step of delivering at least one further series of electrical current pulses, after delivering said first electrical defibrillation pulse, and after determining the output status of the heart, and if said determination indicates a continued existence of arrythmia or the presence of a low pressure in the heart indicative of inadequate cardiac output.

93. The method of claim 91, in which the electrical current pulses are timed to coincide with the natural pumping of the patient's atria.

94. The method of claim 92, in which said step of determining the output status of the heart comprises initiation by said output control means of an adjustment of the characteristics of said electrical current pulses according to said determined output status.

95. A method for providing hemodynamic output of a heart during arrythmia, comprising the steps of:

(a) positioning a plurality of electrodes within portions of a patient's body proximate the patient's heart for delivery or receipt of electrical pulses transmitted through portions of the patient's upper body and heart;

(b) providing means for detecting the presence of arrhythmia in the patient;

(c) detecting the presence of arrhythmia or low cardiac output in the patient;

(d) delivering a first series of electrical current pulses for a first period of time, through the patient's heart, via electrodes after detecting said arrhythmia, said first series of electrical current pulses comprising at least one electrical current pulse having a voltage level suitable for defibrillating the patient's heart; and (e) delivering a second series of electrical current pulses for a first period of time, through a portion of the patient's upper body and heart, via said electrodes after detecting arrhythmia; said second series of electrical current pulses comprising a plurality of pulses having a voltage level less than a normal defibrillation voltage level but enough to force hemodynamic activity by contraction of the patient's heart and to facilitate a minimum level of cardiac output.

96. The method of claim 95 further comprising the step of determining the output status of the heart.

97. The method of claim 95 in which the arrythmia is of an asystole type relating to absence of cardiac contraction and leading to cardiac arrest.

98. The method of claim 95, in which the pulse widths of said second series pulses are between about 1 ms and about 50 ms.

99. The method of claim 95, in which the pulse widths of said second series pulses are greater than about 1 ms and less than about 20 ms.

100. A method for conducting emergency electrical cardiac output in a human, comprising the steps of:

(a) providing means for detecting the presence of arrhythmia in the patient;

(b) detecting the presence of arrhythmia in the patient;

(c) delivering electrical current pulses through the patient's body to the patient's heart via electrodes, after detecting arrhythmia, at a voltage level of less than a defibrillating voltage level, to force contraction in the patient's heart and to facilitate a minimum level of cardiac output until cessation of the arrhythmia or until other medical intervention is provided; and (d) providing further medical intervention by delivering a series of defibrillation pulses through the patient's body, said series comprising at least one electrical current pulse having a voltage level sufficient to defibrillate the patient's heart.

101. The method of claim 100 in which the electrical current pulses are delivered ata rate of less than about 200 pulses per minute.

\* \* \* \* \*